(12) United States Patent
Shalaby et al.

(10) Patent No.: US 6,794,364 B2
(45) Date of Patent: *Sep. 21, 2004

(54) IONIC MOLECULAR CONJUGATES OF N-ACYLATED DERIVATIVES OF POLY(2-AMINO-2-DEOXY-D-GLUCOSE) AND POLYPEPTIDES

(75) Inventors: Shalaby W. Shalaby, Anderson, SC (US); Steven A. Jackson, Newtonville, MA (US); Francis X. Ignatious, Exton, PA (US); Jacques-Pierre Moreau, Upton, MA (US); Ruth M. Russell, Dublin (IE)

(73) Assignee: Kinerton Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 10/251,018

(22) Filed: Sep. 20, 2002

(65) Prior Publication Data

US 2003/0092800 A1 May 15, 2003

Related U.S. Application Data

(62) Division of application No. 09/169,423, filed on Oct. 9, 1998, now Pat. No. 6,479,457, which is a continuation-in-part of application No. 08/929,363, filed on Sep. 9, 1997, now Pat. No. 5,821,221, which is a division of application No. 08/468,947, filed on Jun. 6, 1995, now Pat. No. 5,665,702.

(51) Int. Cl.[7] ............................................. A61K 38/00
(52) U.S. Cl. ................................. 514/16; 514/2; 514/9; 514/11
(58) Field of Search ........................... 514/2, 9, 11, 16

(56) References Cited

U.S. PATENT DOCUMENTS

| 4,675,189 A | | 6/1987 | Kent et al. | |
|---|---|---|---|---|
| 4,767,628 A | | 8/1988 | Hutchinson | |
| 5,271,945 A | | 12/1993 | Yoshioka et al. | |
| 5,665,702 A | * | 9/1997 | Shalaby et al. | 514/9 |
| 5,821,221 A | * | 10/1998 | Shalaby et al. | 514/9 |
| 6,479,457 B2 | | 11/2002 | Shalaby et al. | |

FOREIGN PATENT DOCUMENTS

| EP | 0 482 649 A2 | 4/1992 |
|---|---|---|
| EP | 0 486 959 A1 | 5/1992 |
| EP | 0 525 813 A1 | 2/1993 |
| EP | 0 643 963 A | 3/1995 |
| EP | 0 544 000 A1 | 6/1995 |
| HU | 212662 B | 8/1994 |
| JP | 63 258579 A | 10/1988 |
| WO | 95/04752 | 12/1995 |
| WO | 96/04927 | 2/1996 |
| WO | 96/39160 | 12/1996 |

OTHER PUBLICATIONS

Song, et al., "Drug Release and Antitumor Characteristics of N–Succinyl–chitosan–mitomycin C as an Implant," 1996. J. Controlled Release 42:93–100.

Domard et al., "Preparation and Characterization of Fully Deacetylated Chitosan", Int. J. Biol. Macromol., 5:49–52, 1983.

Jameela et al., "Cross–linked Chitosan Microspheres as Carriers for Prolonged Delivery of Macromolecular Drugs", J. Biomater. Sci. Polymer Edn., 6:621–632, 1994.

Mima et al., "Highly Deacetylated Chitosan and Its Properties", Journal of Applied Polymer Sciences, 28:1909–1917, 1983.

Song et al., "Pharmacokinetic Characteristics and Antitumor Activity of the N–Succinyl–chitosan–Mitomycin . . . ", Biol. Pharm. Bull, 16:48–54, 1993.

Song et al., "Synthesis and Drug–Release Characteristics of the Conjugates of Mitomycin C with N–Succinyl chitosan and Carboxymethyl–chitin", Chem. Pharm. Bull, 40:2822–2825, 1992.

Tokura et al., "Induction of Drug Specific Antibody and the Controlled Release of Drug by 6–0–Carboxymethyl Chitin", Journal of Controlled Release, 28:235–241, 1994.

Watanabe et al., "6–0–Carboxymethyl–Chitin (CM–chitin) as a Drug Carrier", Chem. Pharm. Bull, 38:506–509, 1990.

* cited by examiner

Primary Examiner—Louise N. Leary
Assistant Examiner—Maury Audet
(74) Attorney, Agent, or Firm—Fish & Richardson; Brian R. Morrill; Alan F. Feeney

(57) ABSTRACT

A copolymer comprising an N-acylated derivative, and a composition comprising said copolymer and a polypeptide, said polypeptide comprising at least one effective ionogenic amine, wherein at least 50 percent, by weight, of said polypeptide present in said composition is ionically bound to said polymer.

2 Claims, No Drawings

IONIC MOLECULAR CONJUGATES OF N-ACYLATED DERIVATIVES OF POLY(2-AMINO-2-DEOXY-D-GLUCOSE) AND POLYPEPTIDES

CROSS REFERENCE TO RELATED APPLICATION

This application is a divisional application of application, application Ser. No. 09/169,423, filed Oct. 9, 1998, now U.S. Pat. No. 6,479,457 which is a continuation-in-part application of application Ser. No. 08/929,363, now U.S. Pat. No. 5,821,221, filed Sep. 9, 1997, which is a divisional application of application Ser. No. 08/468,947, now U.S. Pat. No. 5,665,702, filed Jun. 6, 1995.

BACKGROUND OF THE INVENTION

Polymer drug delivery systems have been developed for the controlled release of pharmaceutical polypeptides. For example, synthetic polyesters such as poly(DL-lactic acid), poly(glycolic acid), poly(lactic-glycolic acid), and poly(∈-caprolactone) have been used in the form of microcapsules, films, or rods to release biologically active polypeptides. See e.g., U.S. Pat. Nos. 4,767,628 and 4,675,189 and PCT Application No. WO 94/00148.

In addition to the synthetic polymeric chains, natural polymers and their derivatives have been used as components in similar sustained release compositions that dissociate by enzymatic degradation. One example of such natural polymers are those based on chitin, a poly(N-acetylglucosamine). However, since chitin is water insoluble, others have examined solubilizable derivatives which are based primarily on a partially deacetylated chitin, e.g., chitosan. See e.g., Sanford, P. A. et al., Eds., Advances in Chitin & Chitosan (1992). Although chitosan can be found in some fungi, the production of biodegradable chitosan is generally performed synthetically. See Mima, et. al., J. Appl. Polym. Sci. 28 1909–1917 (1983). Synthetic derivatives of chitosan have also been prepared to alter the polymer's in vivo biological characteristics. See Muzzarelli, et al., Carbohydrate Res. 207:199–214 (1980).

The use of chitin, as well as chitin derivatives, has been proposed in a number of drug delivery systems. See, e.g., European Patent Application Nos. 486,959, 482,649, 525, 813 A1, and 544,000 A1; and U.S. Pat. No. 5,271,945.

SUMMARY OF THE INVENTION

In one aspect, the present invention features a copolymer including an N-acylated derivative of poly(2-amino-2-deoxy-D-glucose), wherein between 1 and 50 percent of the free amines of the poly(2-amino-2-deoxy-D-glucose) are acylated with a first acyl group, the first acyl group is $COE_1$ where $E_1$ is selected from the group consisting of $C_{3-33}$ carboxyalkyl, $C_{3-33}$ carboxyalkenyl, $C_{7-39}$ carboxyarylalkyl, and $C_{9-39}$ carboxyarylalkenyl, and between 50 and 99 percent of the free amines of the poly(2-amino-2-deoxy-D-glucose) are acylated with a second acyl group, the second acyl group is $COE_2$ where $E_2$ is selected from the group consisting of $C_{1-30}$ alkyl, $C_{2-30}$ alkenyl, $C_{6-37}$ arylalkyl, and $C_{8-37}$ arylalkenyl, provided at least one of the free amines of the derivative is acylated with the first acyl group.

The copolymer preferably has a molecular weight of about 3,000 to 90,000 daltons. In other preferred embodiments, over 90 percent of the free amines of the poly(2-amino-2-deoxy-D-glucose) are acylated with either the first acyl group or the second acyl group. Preferably, between 10 and 30 percent of the free amine of the poly(2-amino-2-deoxy-D-glucose) are acylated with the first acyl group. Some of the free hydroxy groups (e.g., between 1 and 30 percent) of the derivative may be acylated with either the first acyl group or the second acyl group.

In a preferred embodiment, the copolymer is of the formula:

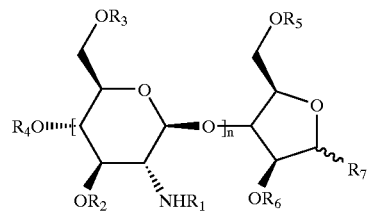

wherein:
$R_1$, for each individual repeat unit, is selected from the group consisting of first acyl group, second acyl group, and H;

$R_2$, for each individual repeat unit, is selected from the group consisting of first acyl group, second acyl group, and H;

$R_3$, for each individual repeat unit, is selected from the group consisting of first acyl group, second acyl group, and H;

$R_4$ is selected from the group consisting of first acyl group, second acyl group, and H;

$R_5$ is selected from the group consisting of first acyl group, second acyl group, and H;

$R_6$ is selected from the group consisting of first acyl group, second acyl group, and H;

$R_7$ is selected from the group consisting of COH and $CH_2OR_8$;

$R_8$ is selected from the group consisting of first acyl group, second acyl group, and H;

n is between 2 and 200; and for between 1 and 50 percent of the repeat units, $R_1$ is first acyl group, and for between 50 and 99 percent of the repeat units, $R_1$ is second acyl group, provided that for at least one of the repeat units, $R_1$ is first acyl group.

The terms $COE_1$ and $COE_2$ stand for —C=O·$E_1$ and —C=O·$E_2$, respectively. The substituents carboxyalkyl, carboxyalkenyl, carboxyarylalkyl, and carboxyarylalkenyl may contain 1–4 carboxylic acid functionalities. Examples of the first acyl group include, but are not limited to, succinyl, 2-($C_{1-30}$ alkyl)succinyl, 2-($C_{2-30}$ alkenyl)succinyl, maleyl, phthalyl, glutaryl, and itaconyl. Examples of the second acyl group include but are not limited to, acetyl, benzoyl, propionyl, and phenylacetyl.

The present invention also features a composition including the above copolymer and a polypeptide, the polypeptide comprising at least one effective ionogenic amine, wherein at least 50 percent, by weight, of the polypeptide present in the composition is ionically bound to the polymer. Preferably, the composition comprises between 5 and 50 percent, by weight, of the polypeptide.

Preferred embodiments of the present invention include a copolymer wherein the first acyl group is succinyl and the second acyl group is acetyl and $R_7$ is COH or $CH_2OH$; a composition comprising said copolymer of claim 1 and H-β-D-Nal-Cys-Tyr-D-Trp-Lys-Val-Cys-Thr-$NH_2$ or a pharmaceutically acceptable salt thereof, wherein the two Cys are bonded by a disulfide bond, where at least 50 percent, by weight, of H-β-D-Nal-Cys-Tyr-D-Trp-Lys-Val-Cys-Thr-NH₂ or a pharmaceutically acceptable salt thereof, present in said composition is ionically bound to said copolymer; a composition comprising the foregoing copolymer and a peptide selected from the group consisting of

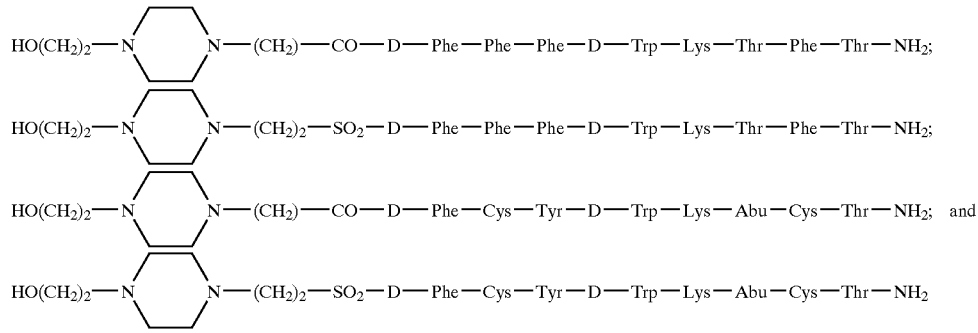

or a pharmaceutically acceptable salt thereof, where at least 50 percent, by weight, of said peptide or a pharmaceutically acceptable salt thereof present in said composition is ionically bound to said copolymer; a composition comprising the foregoing copolymer and a

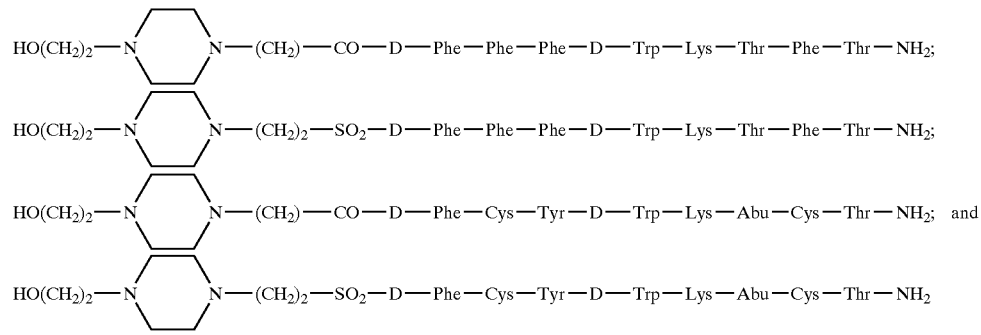

peptide selected from the group consisting of (p-Glu-His-Trp-Ser-Tyr-D-Trp-Leu-Arg-Pro-Gly-NH₂), ([D-Ser(t-Bu)⁶, des-Gly-NH₂¹⁰]-LHRH(1–9)NHEt), ([D-Trp⁶, des-Gly-NH₂¹⁰]-LHRH(1–9)NHEt, ([des-Gly-NH₂¹⁰]-LHRH(1–9)NHEt), ([D-Ser(t-Bu)⁶, Azgly¹⁰]-LHRH), ([D-His(Bzl)⁶, des-Gly-NH₂¹⁰]-LHRH(1–9) NHEt), ([D-Leu⁶, des-Gly-NH₂¹⁰]-LHRH(1–9)NHEt), ([D-Trp⁶, MeLeu⁷, des-Gly-NH₂¹⁰]-LHRH(1–9) NHEt), and ([D-Nal⁶]-LHRH, or a pharmaceutically acceptable salt thereof, where at least 50 percent, by weight, of said peptide or a pharmaceutically acceptable salt thereof, present in said composition is ionically bound to said copolymer; a composition comprising the foregoing copolymer and parathyroid hormone, an analogue thereof or a pharmaceutically acceptable salt thereof, where at least 50 percent, by weight, of parathyroid hormone, an analogue thereof or a pharmaceutically acceptable salt thereof, present in said composition is ionically bound to said copolymer.

Further preferred embodiments of the present invention include a copolymer wherein the first acyl group is glutaryl and the second acyl group is propionyl and R₇ is COH or CH₂OH; a composition comprising the foregoing copolymer and H-β-D-Nal-Cys-Tyr-D-Trp-Lys-Val-Cys-Thr-NH₂, wherein the two Cys are bonded by a disulfide bond, where at least 50 percent, by weight, of H-β-D-Nal-Cys-Tyr-D-Trp-Lys-Val-Cys-Thr-NH₂, present in said composition is ionically bound to said copolymer; a composition comprising the foregoing copolymer and a peptide selected from the group consisting of or a pharmaceutically acceptable salt thereof, where at least 50 percent, by weight, of said peptide or a pharmaceutically acceptable salt thereof present in said composition is ionically bound to said copolymer; a composition comprising the foregoing copolymer and a peptide selected from the group consisting of (p-Glu-His-Trp-Ser-Tyr-D-Trp-Leu-Arg-Pro-Gly-NH₂), ([D-Ser(t-Bu)⁶, des-Gly-NH₂¹⁰]-LHRH (1–9)NHEt), ([D-Trp⁶, des-Gly-NH₂¹⁰]-LHRH(1–9)NHEt, ([des-Gly-NH₂¹⁰]-LHRH(1–9)NHEt), ([D-Ser(t-Bu)⁶, Azgly¹⁰]-LHRH), ([D-His(Bzl)⁶, des-Gly-NH₂¹⁰]-LHRH (1–9)NHEt), ([D-Leu⁶, des-Gly-NH₂¹⁰]-LHRH(1–9)NHEt), ([D-Trp⁶, MeLeu⁷, des-Gly-NH₂¹⁰]-LHRH(1–9)NHEt), and ([D-Nal⁶]-LHRH, or a pharmaceutically acceptable salt thereof, where at least 50 percent, by weight, of said peptide or a pharmaceutically acceptable salt thereof, present in said composition is ionically bound to said copolymer; and a composition comprising the foregoing copolymer and parathyroid hormone, an analogue thereof or a pharmaceutically acceptable salt thereof, where at least 50 percent, by weight, of parathyroid hormone, an analogue or a pharmaceutically acceptable salt thereof, present in said composition is ionically bound to said copolymer.

Examples of suitable polypeptides include growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), growth hormone (GH), amylin, tachykinins, secretin, parathyroid hormone (PTH), encephalon, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH and biologically active analogs thereof. The term "biologically active analogs" is used herein to cover naturally occurring, recombinant, and synthetic peptides, polypeptides, and proteins having physiological or therapeutic activity. In general, the term covers all fragments and derivatives of a peptide, protein, or a polypeptide that exhibit a qualitatively similar agonist or antagonist effect to that of the unmodified, or naturally occurring peptide, protein, or polypeptide, e.g., those in which one or more of the amino acid residues occurring in the natural compounds are substituted or deleted, or in which the N- or C-terminal residues has been structurally modified. The term effective ionogenic amine refers to a free amine present on the polypeptide which is capable of forming an ionic bond with the free carboxylic groups on the copolymer.

Examples of other somatostatin analogs include, but are not limited to, the following somatostatin analogs which are disclosed in the above-cited references:

H-β-D-Nal-Cys-Tyr-D-Trp-Lys-Val-Cys-Thr-NH$_2$ acetate salt (also known as SOMATULINE™), where the two Cysteines are bonded by a disulfide bond;
H—D-Phe-Cys-Phe-D-Trp-Lys-Thr-Cys-β-Nal-NH$_2$;
H—D-Phe-Cys-Tyr-D-Trp-Lys-Thr-Cys-β-Nal-NH$_2$;
H—D-β-Nal-Cys-Phe-D-Trp-Lys-Thr-Cys-Thr-NH$_2$;
H—D-Phe-Cys-Tyr-D-Trp-Lys-Thr-Pen-Thr-NH$_2$;
H—D-Phe-Cys-Phe-D-Trp-Lys-Thr-Pen-Thr-NH$_2$;
H—D-Phe-Cys-Tyr-D-Trp-Lys-Thr-Pen-Thr-OH;
H—D-Phe-Cys-Phe-D-Trp-Lys-Thr-Pen-Thr-OH;
H-Gly-Pen-Phe-D-Trp-Lys-Thr-Cys-Thr-OH;
H-Phe-Pen-Tyr-D-Trp-Lys-Thr-Cys-Thr-OH;
H-Phe-Pen-Phe-D-Trp-Lys-Thr-Pen-Thr-OH;
H—D-Phe-Cys-Phe-D-Trp-Lys-Thr-Cys-Thr-ol;
H—D-Phe-Cys-Phe-D-Trp-Lys-Thr-Cys-Thr-NH$_2$;
H—D-Trp-Cys-Tyr-D-Trp-Lys-Val-Cys-Thr-NH$_2$;
H—D-Trp-Cys-Phe-D-Trp-Lys-Thr-Cys-Thr-NH$_2$;
H—D-Phe-Cys-Tyr-D-Trp-Lys-Val-Cys-Thr-NH$_2$;
H—D-Phe-Cys-Tyr-D-Trp-Lys-Val-Cys-Trp-NH$_2$;
H—D-Phe-Cys-Tyr-D-Trp-Lys-Val-Cys-Thr-NH$_2$;
Ac-D-Phe-Lys*-Tyr-D-Trp-Lys-Val-Asp*-Thr-NH$_2$ (an amide bridge formed between Lys* and Asp*);
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$–CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg (Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$—D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$—D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
H-Bmp-Tyr-D-Trp-Lys-Val-Cys-Thr-NH$_2$;
H-Bmp-Tyr-D-Trp-Lys-Val-Cys-Phe-NH$_2$;
H-Bmp-Tyr-D-Trp-Lys-Val-Cys-p-Cl-Phe-NH$_2$;
H-Bmp-Tyr-D-Trp-Lys-Val-Cys-β-Nal-NH$_2$;
H—D-β-Nal-Cys-Tyr-D-Trp-Lys-Val-Cys-Thr-NH$_2$;
H—D-Phe-Cys-Tyr-D-Trp-Lys-Abu-Cys-Thr-NH$_2$;
H—D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo(Pro-Phe-D-Trp-N-Me-Lys-Thr-Phe);
cyclo(Pro-Phe-D-Trp-N-Me-Lys-Thr-Phe);
cyclo(Pro-Phe-D-Trp-Lys-Thr-N-Me-Phe);
cyclo(N-Me-Ala-Tyr-D-Trp-Lys-Thr-Phe);
cyclo(Pro-Tyr-D-Trp-Lys-Thr-Phe);
cyclo(Pro-Phe-D-Trp-Lys-Thr-Phe);
cyclo(Pro-Phe-L-Trp-Lys-Thr-Phe);
cyclo(Pro-Phe-D-Trp(F)-Lys-Thr-Phe);
cyclo(Pro-Phe-Trp(F)-Lys-Thr-Phe);
cyclo(Pro-Phe-D-Trp-Lys-Ser-Phe);
cyclo(Pro-Phe-D-Trp-Lys-Thr-p-Cl-Phe);
cyclo(D-Ala-N-Me-D-Phe-D-Thr-D-Lys-Trp-D-Phe);
cyclo(D-Ala-N-Me-D-Phe-D-Val-Lys-D-Trp-D-Phe);
cyclo(D-Ala-N-Me-D-Phe-D-Thr-Lys-D-Trp-D-Phe);
cyclo(D-Abu-N-Me-D-Phe-D-Val-Lys-D-Trp-D-Tyr);
cyclo(Pro-Tyr-D-Trp-t-4-AchxAla-Thr-Phe);
cyclo(Pro-Phe-D-Trp-t-4-AchxAla-Thr-Phe);
cyclo(N-Me-Ala-Tyr-D-Trp-Lys-Val-Phe);
cyclo(N-Me-Ala-Tyr-D-Trp-t-4-AchxAla-Thr-Phe);
cyclo(Pro-Tyr-D-Trp-4-Amphe-Thr-Phe);
cyclo(Pro-Phe-D-Trp-4-Amphe-Thr-Phe);
cyclo(N-Me-Ala-Tyr-D-Trp-4-Amphe-Thr-Phe);
cyclo(Asn-Phe-Phe-D-Trp-Lys-Thr-Phe-Gaba);
cyclo(Asn-Phe-Phe-D-Trp-Lys-Thr-Phe-Gaba-Gaba);

cyclo(Asn-Phe-D-Trp-Lys-Thr-Phe);
cyclo(Asn-Phe-Phe-D-Trp-Lys-Thr-Phe-NH(CH$_2$)$_4$CO);
cyclo(Asn-Phe-Phe-D-Trp-Lys-Thr-Phe-β-Ala);
cyclo(Asn-Phe-Phe-D-Trp-Lys-Thr-Phe-D-Glu)-OH;
cyclo(Phe-Phe-D-Trp-Lys-Thr-Phe);
cyclo(Phe-Phe-D-Trp-Lys-Thr-Phe-Gly);
cyclo(Phe-Phe-D-Trp-Lys-Thr-Phe-Gaba);
cyclo(Asn-Phe-Phe-D-Trp-Lys-Thr-Phe-Gly);
cyclo(Asn-Phe-Phe-D-Trp(F)-Lys-Thr-Phe-Gaba);
cyclo(Asn-Phe-Phe-D-Trp(NO$_2$)-Lys-Thr-Phe-Gaba);
cyclo(Asn-Phe-Phe-Trp(Br)-Lys-Thr-Phe-Gaba);
cyclo(Asn-Phe-Phe-D-Trp-Lys-Thr-Phe(I)-Gaba);
cyclo(Asn-Phe-Phe-D-Trp-Lys-Thr-Tyr(But)-Gaba);
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Tpo-Cys)-OH;
cyclo(Bmp-Lys-Asn-Phe-Phe-D-Trp-Lys-Thr-Phe-Thr-MeLeu-Cys)-OH;
cyclo(Phe-Phe-D-Trp-Lys-Thr-Phe-Phe-Gaba);
cyclo(Phe-Phe-D-Trp-Lys-Thr-Phe-D-Phe-Gaba);
cyclo(Phe-Phe-D-Trp(5F)-Lys-Thr-Phe-Phe-Gaba);
cyclo(Asn-Phe-Phe-D-Trp-Lys(Ac)-Thr-Phe-NH—(CH$_2$)$_3$-CO);
cyclo(Lys-Phe-Phe-D-Trp-Lys-Thr-Phe-Gaba);
cyclo(Lys-Phe-Phe-D-Trp-Lys-Thr-Phe-Gaba);
cyclo(Orn-Phe-Phe-D-Trp-Lys-Thr-Phe-Gaba);
H-Cys-Phe-Phe-D-Trp-Lys-Thr-Phe-Cys-NH$_2$;
H-Cys-Phe-Phe-D-Trp-Lys-Ser-Phe-Cys-NH$_2$;
H-Cys-Phe-Tyr-D-Trp-Lys-Thr-Phe-Cys-NH$_2$; and
H-Cys-Phe-Tyr(I)-D-Trp-Lys-Thr-Phe-Cys-NH$_2$.

A disulfide bridge is formed between the two free thiols (e.g., Cys, Pen, or Bmp residues) when they are present in a peptide; however, the disulfide bond is not shown.

Also included are somatostatin agonists of the following formula:

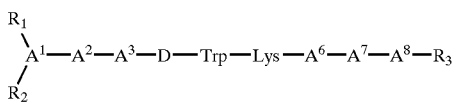

wherein $A^1$ is a D- or L-isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each $R_1$ and $R_2$, independently, is H, lower acyl or lower alkyl; and $R_3$ is OH or NH$_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

Examples of linear agonists to be used in a process of this invention include:

H—D-Phe-p-chloro-Phe-Tyr-D-Trp-Lys-Thr-Phe-Thr-NH$_2$;
H—D-Phe-p-NO$_2$-Phe-Tyr-D-Trp-Lys-Val-Phe-Thr-NH$_2$;
H—D-Nal-p-chloro-Phe-Tyr-D-Trp-Lys-Val-Phe-Thr-NH$_2$;
H—D-Phe-Phe-Phe-D-Trp-Lys-Thr-Phe-Thr-NH$_2$;
H—D-Phe-Phe-Tyr-D-Trp-Lys-Val-Phe-Thr-NH$_2$;
H—D-Phe-p-chloro-Phe-Tyr-D-Trp-Lys-Val-Phe-Thr-NH$_2$; and
H—D-Phe-Ala-Tyr-D-Trp-Lys-Val-Ala-β-D-Nal-NH$_2$.

If desired, one or more chemical moieties, e.g., a sugar derivative, mono or poly-hydroxy $C_{2-12}$ alkyl, mono or poly-hydroxy $C_{2-12}$ acyl groups, or a piperazine derivative, can be attached to the somatostatin agonist, e.g., to the N-terminus amino acid. See PCT Application WO 88/02756, European Application 0 329 295, and PCT Application No. WO 94/04752. An example of somatostatin agonists which contain N-terminal chemical substitutions are:

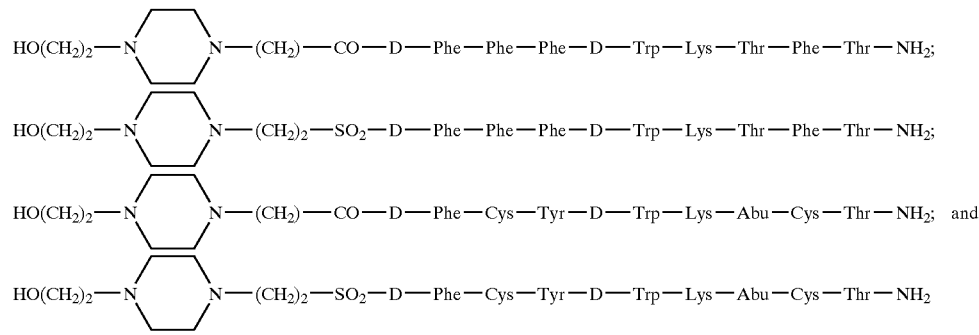

or a pharmaceutically acceptable salt thereof.

Examples of specific LHRH analogues that can be incorporated in a conjugate or composition of this invention are TRYPTORELIN™ (p-Glu-His-Trp-Ser-Tyr-D-Trp-Leu-Arg-Pro-Gly-NH$_2$), buserelin ([D-Ser(t-Bu)$^6$, des-Gly-NH$_2$$^{10}$]-LHRH(1–9)NHEt), deslorelin ([D-Trp$^6$, des-Gly-NH$_2$$^{10}$]-LHRH(1–9)NHEt, fertirelin ([des-Gly-NH$_2$$^{10}$]-LHRH(1–9)NHEt), gosrelin ([D-Ser(t-Bu)$^6$, Azgly$^{10}$]-LHRH), histrelin ([D-His(Bzl)$^6$, des-Gly-NH$_2$$^{10}$]-LHRH(1–9)NHEt), leuprorelin ([D-Leu$^6$, des-Gly-NH$_2$$^{10}$]-LHRH(1–9)NHEt), lutrelin ([D-Trp$^6$, MeLeu$^7$, des-Gly-NH$_2$$^{10}$]-LHRH(1–9)NHEt), nafarelin ([D-Nal$^6$]-LHRH and pharmaceutically acceptable salts thereof.

The release of the polypeptide from the composition may be modified by changing the chemical structure of the composition. Increasing the molecular weight of the polymer will decrease the rate of peptide released from the conjugate. Increasing the number of carboxylic acid groups on the polymer will increase the amount of polypeptide ionically bound to the composition, and consequently, increase the amount of release of the peptide from the conjugate.

The release of the polypeptide may be further modulated through (a) treating the composition with soluble salts of divalent or polyvalent metallic ions of weak acids (e.g., calcium, iron, magnesium, or zinc); (b) coating the particles with a thin, absorbable layer made of a glycolide copolymer or silicone oil in a spherical, cylindrical, or planar configuration; or (c) microencapsulating the composition in an absorbable glycolide copolymer. In one embodiment, the composition comprises between 0.01 and 20 percent, by weight, of a polyvalent metal.

Depending on the choice of polypeptide, the compositions can be used to treat any number of disorders. For example, somatostatin, bombesin, GRP, LHRH, and analogs thereof, have been shown to treat various forms of cancer. Growth factors such as GH, GRF, and GHRP, and analogs thereof, have been shown to stimulate growth in both adolescents and the elderly. Calcitonin, amylin, PTH, and PTHrP, and analogs thereof, have been shown to treat osteoporosis and other bone disorders.

The compositions are designed for parenteral administration, e.g., intramuscular, subcutaneous, intradural, or intraperitoneal injection. Preferably, the compositions are administered intramuscularly.

The compositions of the invention can be in the form of powder or a microparticle to be administered as a suspension with a pharmaceutically acceptable vehicle (e.g., water with or without a carrier substance such as mannitol or polysorbate). The compositions may also be compounded in the form of a rod for parenteral implantation using a trocar, e.g., intramuscular implantation.

The dose of the composition of the present invention for treating the above-mentioned diseases or disorders varies depending upon the manner of administration, the age and the body weight of the subject, and the condition of the subject to be treated, and ultimately will be decided by the attending physician or veterinarian. Such an amount of the composition as determined by the attending physician or veterinarian is referred to herein as a "therapeutically effective amount."

In another aspect, the present invention features a process of synthesizing a copolymer, the process comprising the steps of: reacting chitosan with a weak acid to produce a lower molecular weight polysaccharide; reacting between 1 and 50 percent of the free amines of the lower molecular weight polysaccharide with a first acylating agent, the first acylating agent selected from the group consisting of $C_4$–$C_{34}$ polycarboxyalkane, $C_4$–$C_{34}$ polycarboxyalkene, $C_8$–$C_{40}$ polycarboxyarylalkane, $C_{10}$–$C_{40}$ polycarboxyarylalkene, or an acylating derivative thereof; and reacting between 50 and 100 percent of the free amine of the lower molecular weight polysaccharide with a second acylating agent, the second acylating agent selected from the group consisting of $C_{2-31}$ monocarboxyalkane, $C_{3-31}$ monocarboxyalkene, $C_{7-38}$ monocarboxyarylalkane, $C_{9-35}$ monocarboxyarylalkene, or an acylating derivative thereof. The reaction of the lower molecular weight polysaccharide with both the first acylating agent and the second acylating agent may be measured with an amine detecting agent (e.g., fluorescamine) to ensure that between 1 and 50 percent of the free amines of the lower molecular weight polysaccharide are acylated with the first acylating agent and between 50 and 99 percent of the free amines of the lower molecular weight polysaccharide are acylated with the second acylating agent. See, e.g., Bailey, P. D., An Introduction to Peptide Chemistry (Wiley, N.Y.)(1990); Oppenheimer, H, et al. Archives Biochem. Biophys. 120:108–118 (1967); Stein, S, Arch. Biochem. Biophys. 155:203–212 (1973).

Reacting chitosan with the weak acid (e.g., nitrous acid) cleaves the polymer, thereby reducing its molecular weight (e.g., 2,500–80,000 daltons). In preferred embodiments, the first acylating group and the second acylating agent are reacted with the lower molecular weight polysaccharide successively, e.g., either the first acylating agent is reacted before the second acylating agent is reacted or the second acylating agent is reacted before the first acylating agent or simultaneously. As a result of the acylation of the free amines, some of the free hydroxy groups of the lower molecular weight polysaccharide may be acylated. The extent of the acylation of the free hydroxy groups may be altered by changing the pH or the solvents or agents used during the acylation reactions, or the acylating agents used.

Examples of acylating derivatives include, but are not limited to, anhydrides and N-acylated heterocycles (e.g., imidazoles and pyrazoles). See e.g., Bodansky, et al., The Practice of Peptide Synthesis, 87–150 (Springer-Verlag, 1984). The agents polycarboxyalkane, polycarboxyalkene, polycarboxyarylalkane, and polycarboxyarylalkene or acylating derivatives thereof contain, or originate from reactants containing, 2–5 carboxylic acid functionalities. The substituents monocarboxyalkane, monocarboxyalkene, monocarboxyarylalkane, and monocarboxyarylalkene contain, or originate from reactants containing, only a single carboxylic acid group. Examples of first acylating agents include, but are not limited to, succinic anhydride, 2-($C_{1-30}$ alkyl)succinic anhydride, 2-($C_{2-30}$ alkenyl)succinic anhydride, maleic anhydride, glutaric anhydride, itaconic anhydride, and phthalic anhydride. Examples of second acylating agents include, but are not limited to, acetic anhydride, benzoic anhydride, N,N'-diacetyl-3,5-dimethylpyrazole, N,N-diacetylimidazole, phenylacetic anhydride, propionic anhydride, and butyric anhydride.

In yet another aspect, the present invention features a process of synthesizing a composition, the process comprising the steps of: reacting chitosan with a weak acid to produce a lower molecular weight polysaccharide; reacting between 1 and 50 percent of the free amines of the lower molecular weight polysaccharide with a first acylating agent, the first acylating agent selected from the group consisting of $C_4$–$C_{34}$ polycarboxyalkane, $C_4$–$C_{34}$ polycarboxyalkene, $C_8$–$C_{40}$ polycarboxyarylalkane, $C_{10}$–$C_{40}$ polycarboxyarylalkene, or an acylating derivative thereof; reacting between 50 and 100 percent of the free amine of the lower molecular weight polysaccharide with a second acylating agent, the second acylating agent selected from the group consisting of $C_{2-31}$ monocarboxyalkane, $C_{3-31}$ monocarboxyalkene, $C_{7-38}$ monocarboxyarylalkane, $C_{9-35}$ monocarboxyarylalkene, or an acylating derivative thereof; neutralizing the acylated lower molecular weight polysaccharide with a base; and mixing the neutralized lower acylated molecular weight polysaccharide with a polypeptide salt, wherein the polypeptide salt comprises at least one ionogenic amine, to form a polypeptide-copolymer ionic conjugate.

The neutralization step preferably renders the lower molecular weight polysaccharide emulsifiable or soluble in water. In preferred embodiments, the base is an inorganic base (e.g., sodium hydroxide). The polypeptide salt is preferably a weak acid salt (e.g, acetate, lactate, or citrate). The ionic conjugate can be isolated by filtering or by centrifuging the resulting mixture.

The conjugates of the invention can easily be made into injectable microspheres or microparticles, and implantable films or rods, without the need to utilize processing that entails multiphase emulsions. Preferably, the microparticles are manufactured by (a) dissolving the composition in an aprotic, water miscible organic solvent; (b) mixing the organic solvent in water; and (c) isolating the microparticles from the water. In preferred embodiments, the organic solvent is chosen from the group of acetone, acetonitrile, tetrahydrofuran, dimethylformamide, and dimethyl ethylene glycol.

Other features and advantages of the present invention will be apparent from the detailed description and from the claims.

DETAILED DESCRIPTION OF THE INVENTION

The synthesis and use of the copolymer and copolymer-polypeptide ionic conjugates of this invention are well within the ability of a person of ordinary skill in the art. Unless defined otherwise, all technical and scientific terms used herein have the same meaning as commonly understood by one of ordinary skill in the art to which this invention belongs. Also, all publications, patent applications, patents, and other references mentioned herein are incorporated by reference.

It is believed that one skilled in the art can, based on the description herein, utilize the present invention to its fullest extent. The following specific embodiments are, therefore, to be construed as merely illustrative, and not limitative of the remainder of the disclosure in any way whatsoever.

EXAMPLE 1

Depolymerization of Chitosan

Chitosan (Protan, Inc., Portsmouth, N.H.) is dissolved in aqueous acetic acid by stirring with a mechanical stirrer for one day. Nitrogen gas is bubbled through the solution, while an aqueous solution of sodium nitrite is added. After a half hour, the solution is filtered through a sintered glass funnel, under reduced pressure, to remove insoluble particles which are present in the initial chitosan solution. To the filtered solution is added an aqueous solution of NaOH, and the solution is vigorously stirred in methanol to precipitate the polymer. The resulting precipitate is then filtered and alternately washed five times with water and methanol. The precipitate is then dried in a vacuum oven at 60° C. for two days. The depolymerized chitosan comprises an aldehyde group at one end of the chain. The aldehyde end group may be reduced to a primary hydroxyl group by reaction $NaBH_4$. The depolymerized product can be analyzed by gel permeation chromatography (GPC) to determine both its molecular weight and molecular weight distribution (MWD) in comparison to Pullulan reference standards. NMR (nuclear magnetic resonance) and IR (infra-red) studies can be used to determine the amount of N-acetylation on the depolymerized product.

EXAMPLE 2

Partial Succinylation of Depolymerized Chitosan

The depolymerized chitosan from Example 1 is dissolved in 0.1M aqueous acetic acid. To this solution, methanol is added followed by the addition of a solution of succinic anhydride in acetone. The resulting solution is stirred at room temperature for 24 hours. Upon completion of the succinylation, the solution is then precipitated into aqueous acetone. The resulting precipitate is collected by centrifugation and washed five times with methanol. The precipitate is then dissolved in 0.5M KOH and dialyzed against water to a pH of 7. The dialyzed solution is then concentrated under reduced pressure, precipitated in aqueous acetone, and dried in a vacuum oven at 60° C.

To obtain variable levels of succinylation, the extent of the reaction can be monitored as the acylation proceeds by analyzing for number of unacylated amine groups. The number of unacylated amine groups can be determined by quenching a withdrawn sample of the reaction mixture with an amine detecting agent (e.g., flouorescamine). The amount of amine present can be measured spectrophoretically using a standard curve for the copolymer. Additionally, succinic anhydride, thus, can be added successively until the desired acylation percentage is achieved The exact degree of succinylation of the purified product can be determined using $^1H$ NMR spectroscopy and conductometric titration.

EXAMPLE 3

Acetylation of the N-succinylated Chitosan

The partial succinylated sample from Example 2 is dissolved in 0.1M aqueous acetic acid. To this solution, methanol and acetic anhydride is then added, and the reaction mixture is stirred at room temperature for one day. This solution is then precipitated in aqueous acetone. The resulting precipitate is collected by centrifugation and washed five times with methanol. The precipitate is then dissolved in 0.1N KOH and is dialyzed against water to a pH of 7. The final solution is lyophilized to obtain the final product. The acylation procedure can be measured spectrophoretically as discussed in Example 2, and the exact degree of acylation of the purified product can be determined using $^1H$ NMR spectroscopy and conductometric titration.

EXAMPLE 4

Preparation of poly(N-acyl-D-glucosamine)-peptide ionic conjugate

The N-succinylated chitosan potassium salt of Example 3 is dissolved in water. An aqueous solution of the acetate salt of the somatostatin polypeptide analog SOMATULINE™ (D-Nal-c[Cys-Tyr-D-Trp-Lys-Val-Cys]-Thr-$NH_2$; Kinerton, Dublin, Ireland) is added to the stirred polymer solution. A precipitate forms and is filtered and dried in a vacuum oven at 40° C.

The polypeptide content of the resulting ionic conjugate can be determined by the difference between the amount of initial peptide added and the amount of free residual peptide contained in the filtrate and rinse solution. The peptide content of the resulting ionic conjugate can be determined by comparing the carbon/nitrogen ratio of the initial N-succinylated chitosan with that of the resulting ionic conjugate. GPC analysis can be used to determine molecular weight and MWD, differential scanning calorimetry (DSC) to determine thermal properties and NMR and IR for chemical identity.

EXAMPLE 5

Homogeneous Depolymerization of Chitosan

Chitosan (Aldrich, Sigma-Aldrich Co. Ltd., Gillingham, Dorset, England, high molecular weight, 10 g) was dissolved in 1L of 0.1M aqueous acetic acid (acetic acid, min. 99.8%, Riedel-de Haën, article number 33209) in a 2L glass beaker with stirring at about 144 rpm using a Heidolph mechanical stirrer (model RZR 2102, Kelheim, Germany). Dissolution was complete within ~4 hours. The inherent viscosity, $\eta_{inh}$, of the final depolymerized chitosan was shown to be dependent on the concentration of sodium nitrite and the time given for depolymerization, $t_{depoly}$, (Table 1). Inherent viscosity, $\eta_{inh}$, was determined using a Cannon-Fenske routine Ubbelodhe viscometer (Poulten Selfe & Lee ltd., number 50 of constant 0.003890(mm²/s)/s at 40° C.) with 0.1M acetic acid as solution.

TABLE 1

| NaNO$_2$ (g) | T$_{depolym}$ (min) | Yield (%) | $\eta_{inh}$ (DL/g) |
|---|---|---|---|
| 0.76 | 35 | 90.8 | 1.52 |
| 0.76 | 45 | 87.6 | 0.98 |
| 0.76 | 55 | 85.1 | 0.65 |
| 0.152 | 30 | 76.7 | 0.33 |
| 0.304 | 30 | 22.0 | 0.23 |
| 0.304 | 90 | No ppt. | — |

Sodium nitrite (Aldrich, Sigma-Aldrich Co. Ltd., Gillingham, Dorset, England) in 5–20 ml de-ionized (DI) water (depending on the mass) was added to the solution. After the required depolymerization time, the solution was filtered as quickly as possible through a sintered glass funnel (25–50μ, Ace Glass Incorporated, Vineland, N.J.) to remove insoluble matter. To the filtered solution was added NaOH (Aldrich) in DI water (ranging from 4.5 g in 100 ml to 20 g in 400 ml) to quench the depolymerizing action of NaNO$_2$. Solution was then added to vigorously stirred methanol (Labscan, HPLC grade, 300 ml) to precipitate the polymer. Suspension was spun at 4,000 rpm at 4° C. for 35 min using a Sorvall RC 5B plus centrifuge. After spinning, the supernatant was decanted off and precipitate was washed with a water/methanol (Labscan, AR grade) mixture (1L, 80:20). Suspension was centrifuged as before, supernatant was again decanted off and depolymerized chitosan was lyophilised in an Edwards Super Modulyo lyophiliser for two days following overnight refrigeration. The depolymerized chitosan was further dried for 1 day in a vacuum oven (Bioblock Scientific, Strasbourg, −22 mmHg at 30° C.).

EXAMPLE 6

Heterogeneous Depolymerization

Chitosan (18.0 g, as before) and NaNO$_2$ (as before) were added to a 1L glass beaker. Trifluoroacetic acid solution (Riedel-de Haën, 23 ml in 600 ml DI water, 0.5M) was added to the beaker and the mixture was stirred using a Heidolph mechanical stirrer (as before). Considerable fizzing was observed on addition of the TFA solution. The solution was filtered on a sintered glass funnel (as before). NaOH solution (13.3 g in 165 ml DI water) was added to the filtered solution. The resulting solution was then added to vigorously stirred methanol (Labscan, HPLC grade, 300 ml). Centrifugation and washing was carried out as per homogeneous depolymerization. Table 2 gives results from a series of depolymerization experiments.

TABLE 2

| NaNO$_2$ (g) | T$_{depolym}$ (min) | Yield (%) | $\eta_{inh}$ (DL/g) |
|---|---|---|---|
| 9.0 | 15 | 24.0 | 0.19 |
| 9.0 | 23 | 20.9 | 0.13 |
| 9.0 | 45 | 16.3 | 0.11 |
| 4.5 | 15 | 69.5 | 0.30 |

With the heterogeneous method, dissolution and depolymerization take place simultaneously making it a faster method. Both methods gave similar yields (Table 1; 0.33 DL/g with a yield of 76.7% and 0.30 DL/g with a yield of 69.1%) but with the heterogeneous method larger quantities of chitosan can be used; 18 g as opposed to 10 g. The dried depolymerized chitosan samples (from examples 5 and 6) with inherent viscosity values in the range 0.23–1.51 DL/g were analysed by $^{13}$C NMR in aqueous CD$_3$COOD using a Bruker Spectrospin 400 NMR spectrometer. Chemical shifts of carbons C$_1$ to C$_6$ are given in Table 3. The chemical shift of a particular carbon increases with the inherent viscosity.

TABLE 3

| C Type | Shift (ppm) |
|---|---|
| C$_1$ | 96.12–99.30 |
| C$_2$ | 54.58–57.44 |
| C$_3$ | 75.20–78.69 |
| C$_4$ | 73.55–76.41 |
| C$_5$ | 68.90–71.80 |
| C$_6$ | 58.74–61.77 |

Elemental analysis was carried out on the depolymerized chitosan samples from examples 5 and 6 (Table 4).

TABLE 4

| | $\eta_{inh}$ (DL/g) | % Nitrogen |
|---|---|---|
| Series of Depolymerized Chitosan samples | 0.11 | 3.07 |
| | 0.13 | 3.50 |
| | 0.19 | 3.40 |
| | 0.30 | 5.42 |
| | 0.33 | 5.87 |
| | 0.98 | 6.78 |
| Low mol. Wt. Chitosan | 8.76 | 7.11 |
| High mol. Wt. Chitosan | 48.50 | 7.42 |

The amino content, that is the fraction of chitosan repeating units containing amino groups was obtained by a metachromatic titration using acid red 88 (Aldrich, dye content ~75%) by following the method outlined by Gummow and Roberts (Beryl. D. Gummow, George A. F. Roberts, Makromol. Chem. 186, 1239–1244 (1985), the contents of which are incorporated herein). Amino content values are given in Table 5.

TABLE 5

| $\eta_{inh}$ (DL/g) | Amino Content |
|---|---|
| 48.9 (Aldrich High mol. wt. Chitosan) | 0.83 |
| 8.76 (Aldrich Low mol. Wt. Chitosan) | 0.78 |
| 0.98 | 0.74 |
| 0.30 | 0.56 |

From % nitrogen values and the amino content values of a series of depolymerized chitosan samples in Tables 4 and 5, it is evident that a decrease in $\eta_{inh}$ is accompanied by a decrease in the amino content indicating deamination with depolymerization.

Calculations For Glutarylation/Propionylations:

The masses of glutaric and propionic anhydrides required for a glutarylation/propionylation reaction are dependent on the desired molar ratio between the two anhydrides, the mass and amino content of depolymerized chitosan used. General equations for the masses of anhydrides for stoichiometric glutarylation/propionylation are given here:

Mass of Glutaric Anhydride (GA) required=Desired GA Fraction×Mass Chitosan×Amino Content×114.1*/161**

*F.W. (GA)
**161=F.W. repeating unit of Chitosan

Mass of Propionic Anhydride (PA) required=Desired PA Fraction×Mass Chitosan×Amino Content×130.14***/161

***F.W. (PA)

EXAMPLE 7A

Glutarylation/Propionylation of Depolymerized Chitosan

Depolymerized chitosan from example 5 with an inherent viscosity of 1.51 DL/g was dissolved in 0.1M acetic acid (4.01 g in 150 ml). The amino content of this sample was not known at the time but it can be assumed that it is between 0.74 for depolymerized chitosan of inherent viscosity 0.98 DL/g and 0.78 for low mol. wt. chitosan from Aldrich (Table 5). Glutaric anhydride (Aldrich, 95%, 6.0 g) and propionic anhydride (Aldrich, 99+% m, 6.0 g) with glutaric anhydride at an approximately 5.7 fold excess and propionic anhydride at an approximately 5.0 fold excess in acetone (Labscan, Dublin, Ireland, AR grade, 29.9 ml, 23.62 g) solution were added to the chitosan solution and left stirring overnight. Resulting solution which was gel-like in nature was poured into acetone (Labscan, AR grade, 200 ml) to induce precipitation. Dispersion was spun at 4000 rpm at about 4° C. for about 25 min. After spinning, supernatant was washed with methanol (Labscan, HPLC grade, 600 ml) and spun as before. Supernatant was decanted off and product was lyophilized following overnight refrigeration. Because of the high excess of anhydride used, the lyophilized product was washed by redissolving in 0.2M NaOH solution, filtering to remove insoluble matter and precipitation in methanol (Labscan, HPLC grade, 300 ml). After spinning at 4000 rpm at about 4° C. for about 25 min, supernatant was decanted off and the product was dried by lyophilization (2 days) and vacuum dried for 1 day. % Nitrogen in the final product as determined by elemental analysis was 3.92%.

EXAMPLE 7B

Glutarylation/Propionylation of Depolymerized Chitosan

Depolymerized chitosan from example 5 with an inherent viscosity of 0.98 DL/g was dissolved in 0.1M acetic acid (1.23 g in 46 ml). The amino content of this sample was calculated to be 0.74 (Table 5). Glutaric anhydride (Aldrich, 95%, 1.33 g) and propionic anhydride (Aldrich, 99+% m 1.33 g) with glutaric anhydride at an approximately 3.8 fold excess and propionic anhydride at an approximately 3.3 fold excess in acetone (Labscan, AR grade, 10.1 ml, 8 g) solution was added to the chitosan solution and left stirring overnight. Resulting solution was poured into acetone (Labscan, AR grade, 80 ml) to induce precipitation. Dispersion was spun at 4000 rpm at about 4° C. for about 25 min. After spinning, supernatant was washed with methanol (Labscan, HPLC grade, 600 ml) and spun as before. Supernatant was decanted off and product was lyophilized following overnight refrigeration and then vacuum oven dried (1 day). % Nitrogen of this product as determined from elemental analysis was 5.11%.

EXAMPLE 7C

Glutarylation/Propionylation of Depolymerized Chitosan

Depolymerized chitosan from example 5 with an inherent viscosity of 0.98 DL/g was dissolved in 0.1M acetic acid (4.02 g in 150 ml). The amino content of this sample was calculated to be 0.74 (Table 5). Glutaric anhydride (Aldrich, 95%, 4.01 g) and propionic anhydride (Aldrich, 99+% m 4.05 g) with glutaric anhydride at an approximately 3.8 fold excess and propionic anhydride at an approximately 3.3 fold excess in acetone (Labscan, AR grade, 29.4 ml, 23.2 g) solution was added to the chitosan solution and left stirring overnight. Resulting solution was poured into acetone (Labscan, AR grade, 200 ml) to induce precipitation. Dispersion was spun at 4000 rpm at about 4° C. for about 25 min. After spinning, supernatant was washed with methanol (Labscan, HPLC grade, 600 ml) and spun as before. Supernatant was decanted off and product was lyophilized following overnight refrigeration. Because of the high excess of anhydride used, the lyophilized product was washed by redissolving in 0.2M NaOH solution, filtering to remove insoluble matter and precipitation in methanol (Labscan, HPLC grade, 300 ml). After spinning at 4000 rpm at about 4° C. for about 25 min, supernatant was decanted off and the product was dried by lyophilization (2 days) and vacuum dried for 1 day. % Nitrogen of this product as determined from elemental analysis was 5.11%.

EXAMPLE 7D

Glutarylation/Propionylation of Depolymerized Chitosan

Depolymerized chitosan from example 6 with an inherent viscosity of 0.30 DL/g was dissolved in 0.1M acetic acid (4.01 g in 150 ml). The amino content of this sample was calculated to be 0.56. Glutaric anhydride (Aldrich, 95%, 3.0 g) and propionic anhydride (Aldrich, 99+%, 1.0 g) in acetone (Labscan, Dublin, Ireland, AR grade, 29.9 ml, 23.6 g) solution was added to the chitosan solution and left stirring overnight. Resulting solution was poured into acetone (Labscan, AR grade, 200 ml) to induce precipitation. Dispersion was spun at 4000 rpm at about 4° C. for about 25 min. After spinning, supernatant was washed with methanol (Labscan, HPLC grade, 600 ml) and spun as before. Supernatant was decanted off and product was lyophilized for 2 days following overnight refrigeration and vacuum dried for 1 day. % Nitrogen of this product as determined from elemental analysis was 5.29%.

Glutarylation/Propionylation—A Kinetic Study 6.51 grams of chitosan from example 5 of inherent viscosity, 0.98 DL/g and amino content of 0.74 were dissolved in 0.1M aqueous acetic acid (225 ml). A molar ratio of propionic anhydride to glutaric anhydride of 4 was desired in the final product. Glutaric anhydride (Aldrich, 95%, 1.443 g) was dissolved in methanol (10 ml) (Labscan, Dublin, Ireland, HPLC grade) and the solution was added to the chitosan solution with stirring at room temperature. After about 2 hours, a 40 ml aliquot of the reaction mixture was precipitated in acetone (Labscan, Dublin, Ireland, A.R. grade) spun at 2900 rpm at about 4° C. for about 25 min.

Precipitate was washed with methanol (Labscan. HPLC grade) and dried. Another 40 ml aliquot was taken after 4 hours, precipitated, washed and dried as before. Immediately after the 40 ml aliquot was taken (4 hours), propionic anhydride solution (Aldrich, 99+%, 2.6489 g in methanol (Labscan, HPLC grade, 10 ml)) was added to the reaction mixture. After a further 2 hours reaction (equivalent to a total reaction time of 6 hours from the addition of the glutaric anhydride solution), the entire mixture was precipitated in acetone (Labscan, AR grade, 330 ml), dispersion was spun at 4000 rpm at about 4° C. for about 30 min in a Sorvall RC plus centrifuge. After spinning, supernatant was decanted off and cake was washed twice with methanol (Labscan, HPLC grade, 400 ml), lyophilized and vacuum oven dried. A metachromatic titration as mentioned in examples 5 and 6 was carried out on the three modified chitosan samples taken at 2 hours, 4 hours and finally 6 hours. The amino content of these three samples is given in Table 6.

TABLE 6

| Time (hours) | Amino Content |
|---|---|
| 2 | 0.91 |
| 4 | 0.43 |
| 6 | 0.10 |

EXAMPLE 8A

Preparation of Poly(N-propionylated, N-glutarylated, N-acetylated-D-glucosamine)-Peptide Ionic Conjugate 1.0038 grams of product from example 7A was dissolved in 20 ml 0.2M NaOH solution. 450 µl of acetic acid was added to the glutarylated/propionylated solution to bring the pH down to ~6. Modified chitosan solution was then added slowly to a solution of 122.9 mg of H-β-D-Nal-Cys-Tyr-D-Trp-Lys-Val-Cys-Thr-$NH_2$ acetate salt (also known as SOMATULINE™), where the two Cysteines are bonded by a disulfide bond (Kinerton ltd., Blanchardstown, Dublin, Ireland, B/N 93K2505DL3, Acetate=12.37%, potency= 82.68%) in 3.73 g DI water and precipitation was observed. The precipitate is also known as a conjugate of the polymer and drug. Dispersion was spun at 2900 rpm at about 4° C. for about 25 min using a Sorvall RT 6000 centrifuge. Supernatant was decanted off and retained for further manipulation. Precipitate was placed in a refrigerator. Acetic acid was added to the retained supernatant until the pH fell to ~4. Further precipitation ensued. Dispersion was spun as before and then stored in fridge. Precipitate from first and second centrifuges were lyophilized, vacuum oven dried and yields obtained were respectively 31.7% (356.9 mg) and 36.4% (409.6 mg) with a combined yield of 68.1%. Elemental analysis was carried out on the combined product. % Nitrogen as determined from elemental analysis for the combined conjugate was 4.60% and using the % nitrogen of 3.92% for product from example 7A, the % loading of SOMATULINE™ was calculated to be 6.7%.

In vivo assay: Conjugate of example 8A was suspended in saline containing Tween® 20 (1%) and injected at 7.5 mg peptide equivalent per rat. SOMATULINE™ levels in rat plasma induced by this conjugate were between a maximum value of 636,757+/−124,759 pg/ml and a minimum value of 863+/−145 pg/ml over a 15 day period, see Table 7.

EXAMPLE 8B

Preparation of Poly(N-propionylated, N-glutarylated, N-acetylated-D-glucosamine)-Peptide Ionic Conjugate 1.0010 grams of product from example 7A was dissolved in 12 ml 0.2M NaOH solution. 250 µl of acetic acid was added to the glutarylated/propionylated solution to bring the pH down to ~6. Modified chitosan solution was then added slowly to a solution of 120.3 mg of SOMATULINE™ (Kinerton ltd., Blanchardstown, Dublin, Ireland, B/N 93K2505DL3, Acetate=12.37%, potency=82.68%) in 2.87 g DI water and precipitation was observed. Because of the lower volume of NaOH solution used, the resulting solution was extremely viscous. Dispersion was spun at 2900 rpm at about 4° C. for about 25 min using a Sorvall RT 6000 centrifuge. Supernatant was decanted off and retained for further manipulation. Precipitate was placed in a refrigerator. Acetic acid was added to the retained supernatant until the pH fell to ~4. Further precipitation ensued. Dispersion was spun as before and then stored in a refrigerator. Precipitate from first and second centrifuges were lyophilized, vacuum oven dried and yields obtained were respectively 53.5% (600.4 mg) and 20.9% (234.8 mg) with a combined yield of 74.4%. Elemental analysis was carried out on the combined product. % Nitrogen as determined from elemental analysis for the combined conjugate was 4.30% and using the % nitrogen of 3.92% for product from example 7A, the % loading of SOMATULINE™ was calculated to be 4.0%.

In vivo assay: Conjugate was suspended in saline containing Tween® 20 (1%) and injected at 7.5 mg peptide equivalent per rat. SOMATULINE™ levels in rat plasma induced by this conjugate were between a maximum value of 545,367+/−69,445 pg/ml and a minimum value of 1134+/−325 pg/ml over a 15 day period, see Table 7.

EXAMPLE 8C

Preparation of Poly(N-propionylated, N-glutarylated, N-acetylated-D-glucosamine)-Peptide Ionic Conjugate 1.0190 grams of example 7B was dissolved in 20 ml 0.2M NaOH solution. 200 µl of acetic acid was added to the glutarylated/propionylated solution to bring the pH down to ~6. Modified chitosan solution was then added slowly to a solution of 102.1 mg of SOMATULINE™ (Kinerton ltd., Blanchardstown, Dublin, Ireland, B/N 93K2505DL3, Acetate=12.37%, potency=82.68%) in 2.56 g DI water and precipitation was observed. Dispersion was spun at 2900 rpm at about 4° C. for about 25 min using a Sorvall RT 6000 centrifuge. Supernatant was decanted off and retained for further manipulation. Precipitate was placed in refrigerator. Acetic acid was added to the retained supernatant until the pH fell to ~4. Further precipitation ensued. Dispersion was spun as before and then stored in a refrigerator. Precipitate from first and second centrifuges were lyophilized, vacuum oven dried and the combined yield obtained was 74% (827.1 mg). % Loading of SOMATULINE™ in this conjugate was taken to be similar to the % Loading of SOMATULINE™ example 4D i.e., 14%.

In vivo assay: Conjugate was suspended in saline containing Tween® 20 (1%) and injected at 7.5 mg peptide equivalent per rat. SOMATULINE® levels in rat plasma induced by this conjugate were between a maximum value of 168.141+/−90,972 pg/ml and a minimum value of 1000 pg/ml over a 9 day period, see Table 7.

EXAMPLE 8D

Preparation of Poly(N-propionylated, N-glutarylated, N-acetylated-D-glucosamine)-Peptide Ionic Conjugate 1.0149 grams of example 7C was dissolved in 15 ml 0.05M NaOH solution. The molarity of the NaOH in this example is lower than that of example 8C. 200 μl of acetic acid was added to the glutarylated/propionylated solution to bring the pH down to ~6. Modified chitosan solution was then added slowly to a solution of 125.2 mg of SOMATULINE™ (Kinerton ltd., Blanchardstown, Dublin, Ireland, B/N 93K2505DL3, Acetate=9.37%, potency=80.68%) in 3.0 g DI water and precipitation was observed. Dispersion was spun at 2900 rpm at about 4° C. for about 25 min using a Sorvall RT 6000 centrifuge. Supernatant was decanted off and retained for further manipulation. Precipitate was placed in fridge. Acetic acid was added to the retained supernatant until the pH fell to ~4. Further precipitation ensued. Dispersion was spun as before and then stored in fridge. Precipitate from first and second centrifuges were lyophilized, vacuum oven dried and the combined yield obtained was only 24% (270 mg). Elemental analysis was carried out on the combined product. % Nitrogen as determined from elemental analysis for the combined conjugate was 6.34% and using the % nitrogen of 5.11% for product from example 7C, the % loading of SOMATULINE™ was calculated to be 14.0%.

In vivo assay: Conjugate was suspended in saline containing Tween® 20 (1%) and injected at 7.5 mg peptide equivalent per rat. SOMATULINE™ levels in rat plasma induced by this conjugate were between a maximum value of 192,419+/−112,621 pg/ml and a minimum value of 1000/ml over a 12 day period, see Table 7.

EXAMPLE 8E

Preparation of Poly(N-propionylated, N-glutarylated, N-acetylated-D-glucosamine)-Peptide Ionic Conjugate 2.0 grams of example 7D was dissolved in 28 ml 0.05M NaOH solution. Chitosan solution was then added slowly to a solution of 246.0 mg of SOMATULINE™ (Kinerton ltd., Blanchardstown, Dublin, Ireland, B/N 93K2505DL3, Acetate=9.37%, potency=80.68%) in 6.0 g DI water and precipitation was observed. Dispersion was spun at 2900 rpm at about 4° C. for about 25 min using a Sorvall RT 6000 centrifuge. Supernatant was decanted off. Precipitate was washed with 24 ml DI water and spun as before. Precipitate was then placed in a refrigerator. Elemental analysis was carried out on the product. % Nitrogen as determined from elemental analysis for the conjugate was 6.6% and using the % nitrogen of 5.29% for product from example 7D. The % loading of SOMATULINE™ was calculated to be 15%.

In vivo assay: Conjugate was suspended in saline containing Tween® 20 (1%) and injected at 3.75 mg peptide equivalent per rat. SOMATULINE™ levels in rat plasma induced by this conjugate were between a maximum value of 145,429±122,743 pg/ml and a minimum value of 500±159/ml over a 10 day period, see Table 7.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

TABLE 7

| Example No. | 6 h | Day 2 | Day 3 | Day 5 | Day 10 | Day 15 |
|---|---|---|---|---|---|---|
| 8A | 538257 ± 43374 | 636757 ± 124759 | 74764 ± 14316 | 43353 ± 2582 | 1996 ± 217 | 863 ± 145 |
| 8B | 495495 ± 67884 | 545367 ± 69445 | 60238 ± 6719 | 42132 ± 4762 | 1448 ± 238 | 1134 ± 325 |
| 8C | 168141 ± 90972 | 114160 ± 48759 | 26174 ± 9103 | 5118 ± 2855 | 88 ± 95 | <21 |
| 8D | 192419 ± 112621 | 175009 ± 107126 | 106996 ± 20387 | 27883 ± 12858 | 1532 ± 1178 | 116 ± 0 |
| 8E* | 145429 ± 122743 | 110486 ± 65496 | 21546 ± 11359 | 11420 ± 4782 | 500 ± 159 | <21 |

*Example 8E was injected at a dose of 3.75 mg of peptide equivalent per rat.

What is claimed is:

1. A composition comprising a copolymer and a peptide which said copolymer is an N-acylated derivative of poly (2-amino-2-deoxy-D-glucose) in which between 1 and 50 percent of the free amines of said poly(2-amino-2-deoxy-D-glucose) are acylated with a first acyl group, said first acyl group is $COE_1$ where $E_1$ is selected from the group consisting of $C_{3-33}$ carboxyalkyl, $C_{3-33}$ carboxyalkenyl, $C_{7-39}$ carboxyarylalkyl, and $C_{9-39}$ carboxyarylalkenyl, and between 50 and 99 percent of the free amines of said poly(2-amino-2-deoxy-D-glucose) are acylated with a second acyl group, said second acyl group is $COE_2$ where $E_2$ is selected from the group consisting of $C_{1-30}$ alkyl, $C_{2-30}$ alkenyl, $C_{6-37}$ arylalkyl, and $C_{8-37}$ arylalkenyl, provided at least one of the free amines of said poly(2-amino-2-deoxy-D-glucose) is acylated with said first acyl group and wherein said peptide is H-β-D-Nal-Cys-Tyr-D-Trp-Lys-Val-Cys-Thr-$NH_2$ or a pharmaceutically acceptable salt thereof, present in said composition is ionically bound to said copolymer, wherein said first acyl group is succinyl and said second acyl group is acetyl.

2. A composition comprising a copolymer and a peptide wherein said copolymer is an N-acylated derivative of poly(2-amino-2-deoxy-D-glucose), in which between 1 and 50 percent of the free amines of said poly(2-amino-2-deoxy-D-glucose) are acylated with glutaryl and between 50 and 99 percent of the free amines of said poly(2-amino-2-deoxy-D-glucose) are acylated with propionyl, provided at least one of the free amines of said poly(2-amino-2-deoxy-D-glucose) is acylated with glutaryl and wherein said peptide is H-β-D-Nal-Cys-Tyr-D-Trp-Lys-Val-Cys-Thr-$NH_2$ or a pharmaceutically acceptable salt thereof, in which the two Cys are bonded by a disulfide bond, where at least 50 percent, by weight, of H-β-D-Nal-Cys-Tyr-D-Trp-Lys-Val-Cys-Thr-$NH_2$ or pharmaceutically acceptable salt thereof, present in said composition is ionically bound to said copolymer.

* * * * *